United States Patent
Huh

(10) Patent No.: US 10,149,509 B2
(45) Date of Patent: Dec. 11, 2018

(54) ERGONOMIC OCCIPITAL TRIANGULAR CUSHION PAD FOR HEAD BANDS

(71) Applicant: OTOS WING CO., LTD., Seoul (KR)

(72) Inventor: Moon Young Huh, Seoul (KR)

(73) Assignee: OTOS WING CO., LTD., Seoul (KR)

( * ) Notice: Subject to any disclaimer, the term of this patent is extended or adjusted under 35 U.S.C. 154(b) by 108 days.

(21) Appl. No.: 15/392,358

(22) Filed: Dec. 28, 2016

(65) Prior Publication Data

US 2018/0177259 A1    Jun. 28, 2018

(51) Int. Cl.
| | |
|---|---|
| *A42B 3/14* | (2006.01) |
| *A42B 3/08* | (2006.01) |
| *A61F 9/06* | (2006.01) |
| *A63B 71/10* | (2006.01) |
| *A42B 3/04* | (2006.01) |

(52) U.S. Cl.
CPC .............. *A42B 3/085* (2013.01); *A42B 3/142* (2013.01); *A61F 9/06* (2013.01); *A63B 71/10* (2013.01)

(58) Field of Classification Search
CPC ........... A42B 3/14; A42B 3/145; A42B 3/225; A42B 3/142; A42B 1/22; A42B 3/222; A42B 3/04
See application file for complete search history.

(56) References Cited

U.S. PATENT DOCUMENTS

| | | | | |
|---|---|---|---|---|
| 9,907,348 B2* | 3/2018 | Huh | .......................... | A42B 3/14 |
| 2005/0138719 A1* | 6/2005 | Huh | .......................... | A42B 3/14 |
| | | | | 2/416 |
| 2006/0080761 A1* | 4/2006 | Huh | .......................... | A42B 3/04 |
| | | | | 2/424 |
| 2006/0185052 A1* | 8/2006 | Huh | .......................... | A61F 9/06 |
| | | | | 2/8.2 |
| 2007/0079417 A1* | 4/2007 | Huh | ........................ | A61F 9/065 |
| | | | | 2/8.2 |
| 2007/0080621 A1* | 4/2007 | Huh | ........................ | A61F 9/062 |
| | | | | 313/402 |
| 2007/0131845 A1* | 6/2007 | Huh | ........................ | A61F 9/067 |
| | | | | 250/206.1 |
| 2007/0152132 A1* | 7/2007 | Huh | .......................... | G01J 1/26 |
| | | | | 250/206 |
| 2007/0220649 A1* | 9/2007 | Huh | ........................ | A61F 9/025 |
| | | | | 2/9 |

(Continued)

FOREIGN PATENT DOCUMENTS

KR         200410449         3/2006

*Primary Examiner* — Robert H Muromoto, Jr.
(74) *Attorney, Agent, or Firm* — Cantor Colburn LLP

(57) ABSTRACT

A cushion pad for head bands, installed at the rear part of a head band worn on a worker's head so as to support the back of the worker's head while adjusting the length of the head band. The cushion pad includes a pad unit having a concave spherical-shaped surface closely adhered to the back of the worker's head and provided with a first prop and second props to support the upper central region and both lower side regions of the back of the worker's head, and an adjustment unit formed at the rear of the center of the pad unit and provided with through holes formed at both sides thereof to receive both rear ends of the head band and a rotary lever between the through holes to pressurize and fix the head band, thus allowing a worker to more conveniently and stably wear a welding mask.

16 Claims, 5 Drawing Sheets

(56) References Cited

U.S. PATENT DOCUMENTS

| | | | |
|---|---|---|---|
| 2007/0250986 A1* | 11/2007 | Zuber | A42B 3/145 2/171 |
| 2008/0120752 A1* | 5/2008 | Huh | A61F 9/067 2/8.1 |
| 2009/0000001 A1* | 1/2009 | Huh | A61F 9/067 2/8.7 |
| 2009/0089908 A1* | 4/2009 | Huh | A61F 9/068 2/8.6 |
| 2009/0320187 A1* | 12/2009 | Petzl | A42B 3/14 2/417 |
| 2010/0095438 A1* | 4/2010 | Moelker | A42B 3/145 2/418 |
| 2010/0132086 A1* | 6/2010 | Huh | A61F 9/061 2/8.2 |
| 2011/0010815 A1* | 1/2011 | Huh | A61F 9/067 2/8.8 |
| 2011/0289659 A1* | 12/2011 | Lanez | A42B 3/145 2/411 |
| 2011/0315734 A1* | 12/2011 | Huh | A45F 5/021 224/676 |
| 2012/0144565 A1* | 6/2012 | Huh | A61B 90/35 2/421 |
| 2012/0144567 A1* | 6/2012 | Huh | A42B 3/14 2/424 |
| 2013/0111648 A1* | 5/2013 | Huh | A42B 3/14 2/181 |
| 2013/0111653 A1* | 5/2013 | Huh | A42B 3/122 2/421 |
| 2015/0074877 A1* | 3/2015 | Huh | A42B 3/225 2/422 |

\* cited by examiner

ERGONOMIC OCCIPITAL TRIANGULAR CUSHION PAD FOR HEAD BANDS

BACKGROUND OF THE INVENTION

Field of the Invention

The present invention relates to an occipital triangular cushion pad for head bands which conveniently supports the back of a worker's head wearing a welding mask and is not easily removed from the worker's head.

Description of the Related Art

In general, a welding mask includes a protective shield to protect worker's face and eyes and a head band to fix the protective shield to the worker's head.

As disclosed in Korean Utility Model Registration No. 0410449 (Publication Date: Mar. 9, 2006), a head band includes a side part fixed along the circumference of a worker's head, and an upper part extending from both sides of the side part to the top of the worker's head, and the rear region of the side part of the head band is cut so that the length of the side part is adjustable according to the circumference of the worker's head. Therefore, an adjustment unit to adjust the length of the head band and a cushion pad are formed at the rear part of the head band. The cushion pad has a function of solving inconvenience on the back of the worker's head caused by the adjustment unit and is stably adhered to the worker's head.

However, the cushion pad is formed to extend in the horizontal direction or to extend in the vertical direction and may not safely surround the back of the worker's head.

Further, the head band is easily removed from the worker's head and, if the worker bends his/her head back, the head band contacts the worker's neck and causes inconvenience.

SUMMARY OF THE INVENTION

Therefore, the present invention has been made in view of the above problems, and it is an object of the present invention to provide an ergonomic occipital triangular cushion pad for head bands which is installed at the rear part of a head band of a welding mask so as to adjust the length of the head band and to stably surround the back of a worker's head wearing the welding mask, and, particularly, supports the shape of the lower part of the worker's head so as to prevent the head band from being removed from the worker's head and matches the horizontal and vertical sizes of the back of the worker's head so as to be stably mounted on the back of the worker's head.

It is another object of the present invention to provide an occipital triangular cushion pad for head bands which ergonomically surrounds the back of a worker's head so as to minimize pressure applied to the worker's head by a head band, and generates stopping power between the worker's head and the head band and a soft contact surface therebetween.

It is another object of the present invention to provide an occipital triangular cushion pad for head bands which is formed by double injection molding using a hard material and a soft material, such as hard urethane and silicone, so as to prevent a head band from sliding on hair.

It is yet another object of the present invention to provide an occipital triangular cushion pad for head bands which is selectively applied to a ski helmet, a bicycle helmet, a motorcycle helmet, virtual reality goggles, a safety helmet, an industrial helmet, a safety face shield and a welding helmet so as to be conveniently worn by a worker.

In accordance with an aspect of the present invention, the above and other objects can be accomplished by the provision of a cushion pad for head bands, installed at the rear part of a head band worn on a worker's head so as to support the back of the worker's head while adjusting the length of the head band, the cushion pad for head bands including a pad unit having a concave spherical-shaped surface closely adhered to the back of the worker's head and provided with a first prop extending from the center of the pad unit to support the upper central region of the back of the worker's head and second props extending from the center of the pad unit to support both lower side regions of the back of the worker's head, and an adjustment unit formed at the rear of the center of the pad unit and provided with through holes formed at both sides thereof to receive both rear ends of the head band and a rotary lever installed at the rear of the middle between the through holes to pressurize and thus fix the head band.

A radius $R1$ of the center of the spherical surface of the pad unit in the leftward and rightward directions may be 70 to 110 mm, and a radius $R2$ of the center of the spherical surface of the pad unit in the upward and downward directions may be 85 to 130 mm.

A radius $R3$ of a curved surface formed between the second props as seen from the bottom may be 35 to 80 mm, and a radius $R4$ of the curved surface as seen from the front may be 50 to 100 mm.

A distance $D1$ from the center of the pad unit to the end of the first prop as seen from the front may be 40 to 80 mm, a distance $D2$ from the center of the pad unit to the lower end of the pad unit between the second props may be 15 to 50 mm, and a distance $D3$ from the center of the pad unit to the lower ends of the second props may be 30 to 70 mm.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
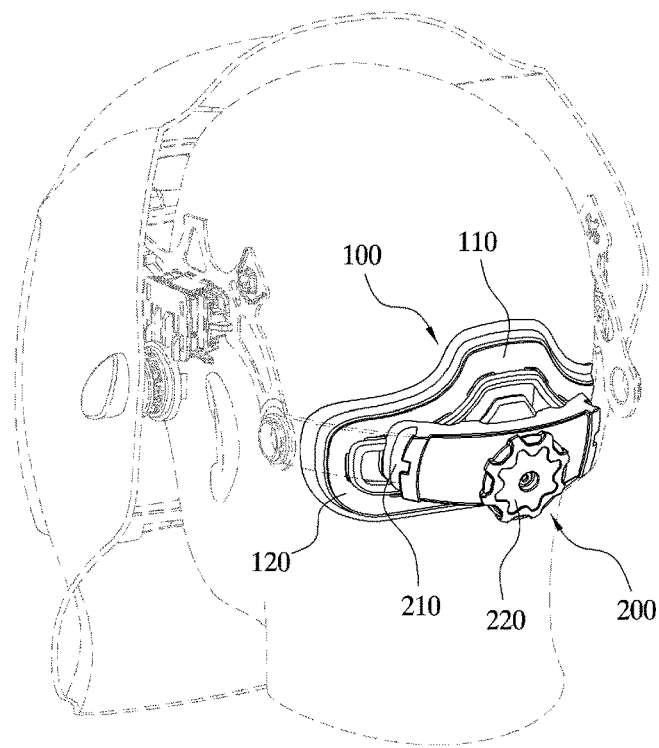
FIG. 1 is a perspective view illustrating a use state of a cushion pad for head bands in accordance with the present invention.

Now, preferred embodiments in accordance with the present invention will be described in detail with reference to the annexed drawings. Terms used in the following description or the claims are not interpreted as having conventional or dictionary meanings and, in order to describe the invention in the best mode by the inventor(s), the definitions of these terms should be determined based on the whole content of this specification.

Therefore, the embodiments stated in the specification and elements illustrated in the drawings have been made only for a better understanding of the present invention and those skilled in the art will appreciate that various modifications, additions, and substitutions to the specific elements are possible, without departing from the scope and spirit of the invention as disclosed in the accompanying claims.

Figure 2:
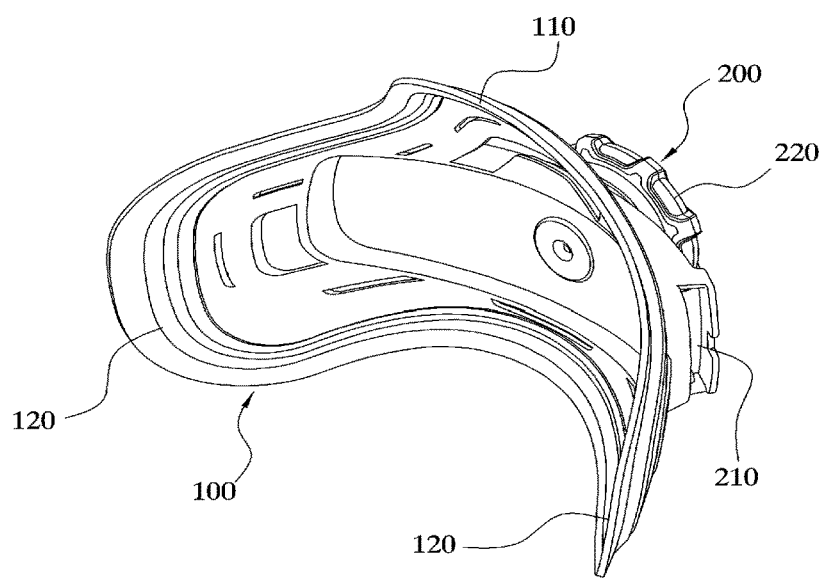
FIGS. 2 and 3 are perspective views illustrating the cushion pad for head bands in accordance with the present invention.
Figure 3:
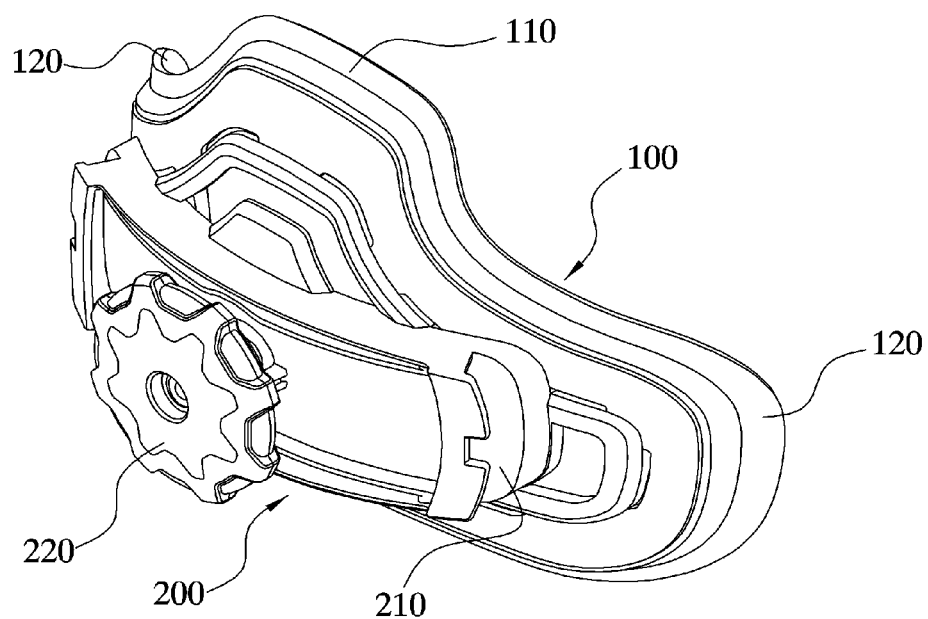
Figure 4:
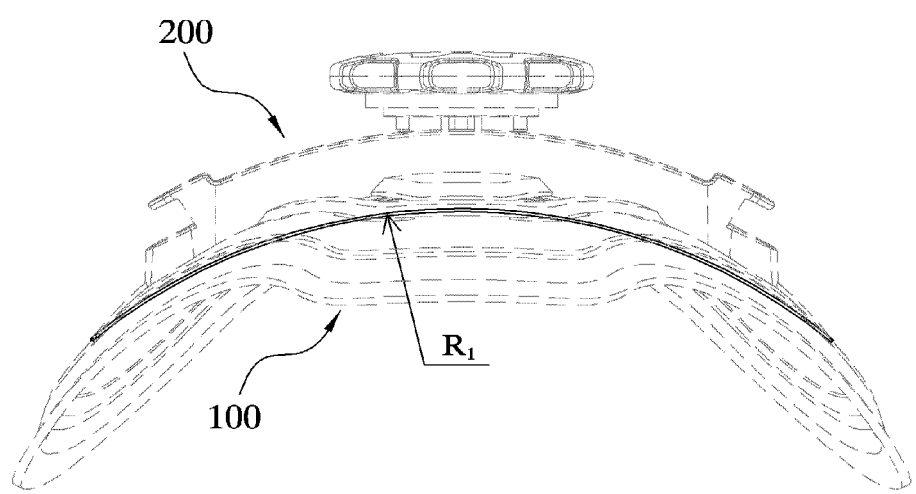
FIGS. 4 to 7 are views illustrating the configuration of the cushion pad for head bands in accordance with the present invention.
Figure 5:
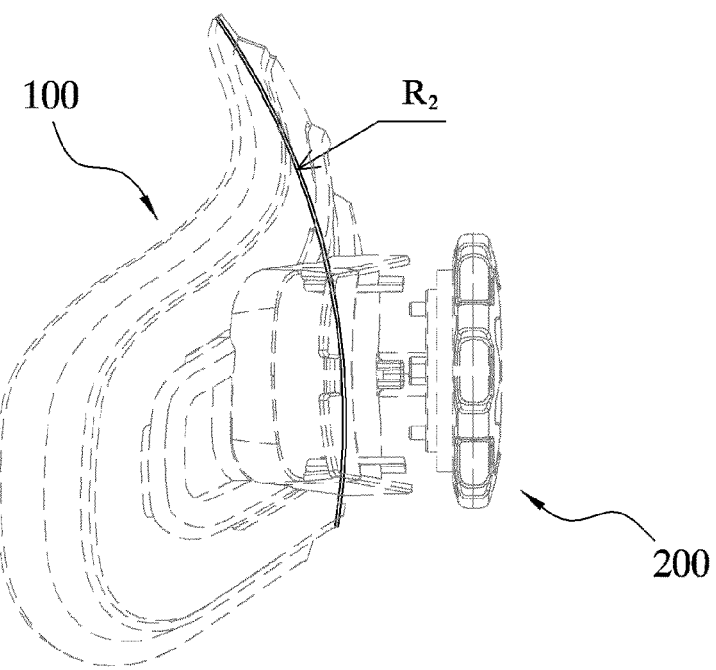
Figure 6:
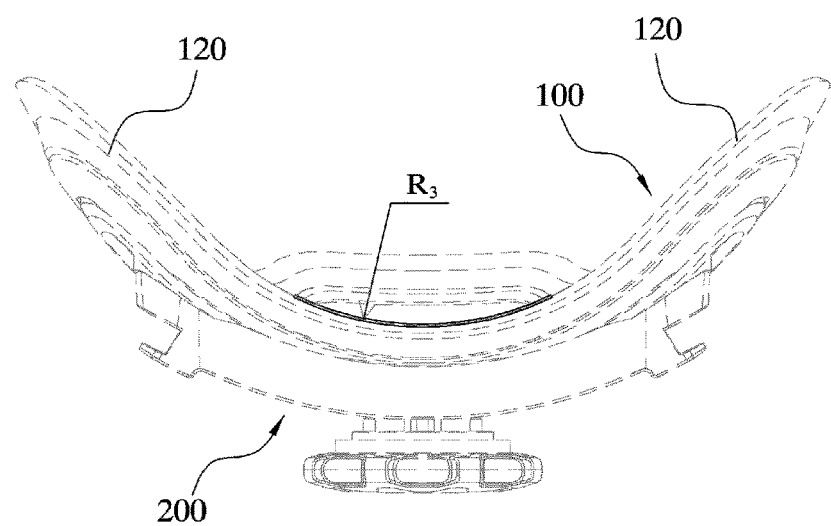
Figure 7:
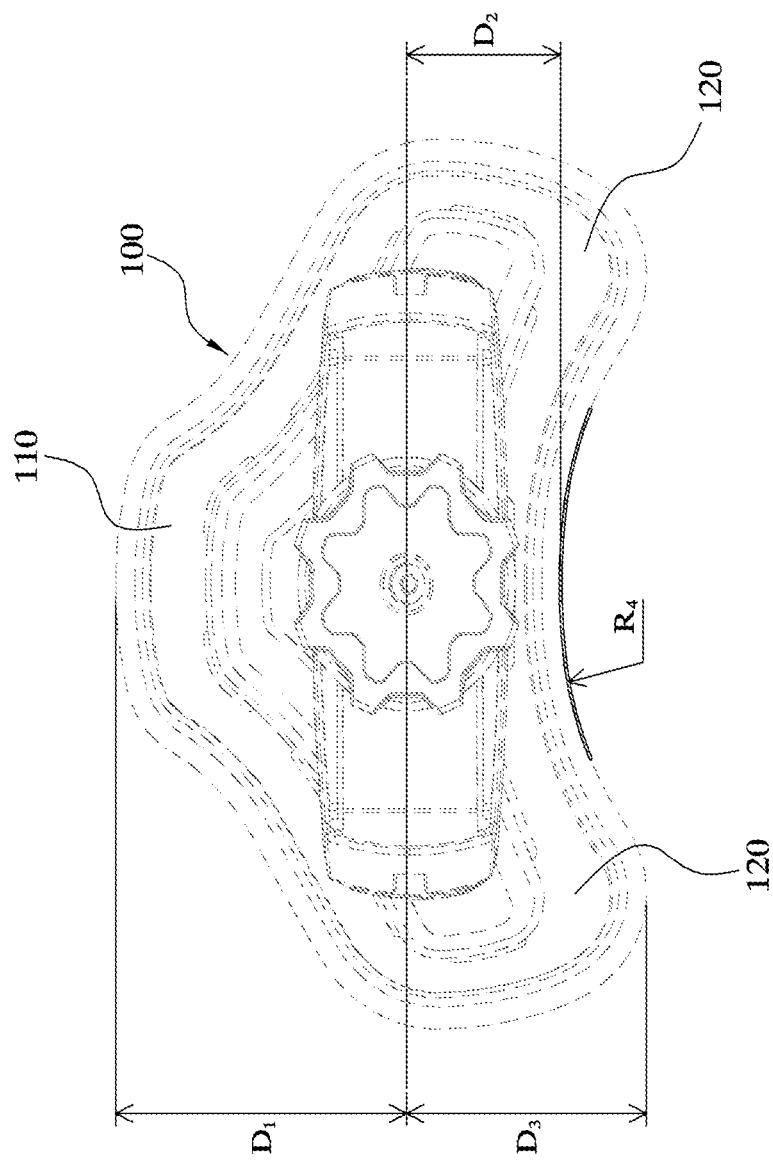
Figure 8:
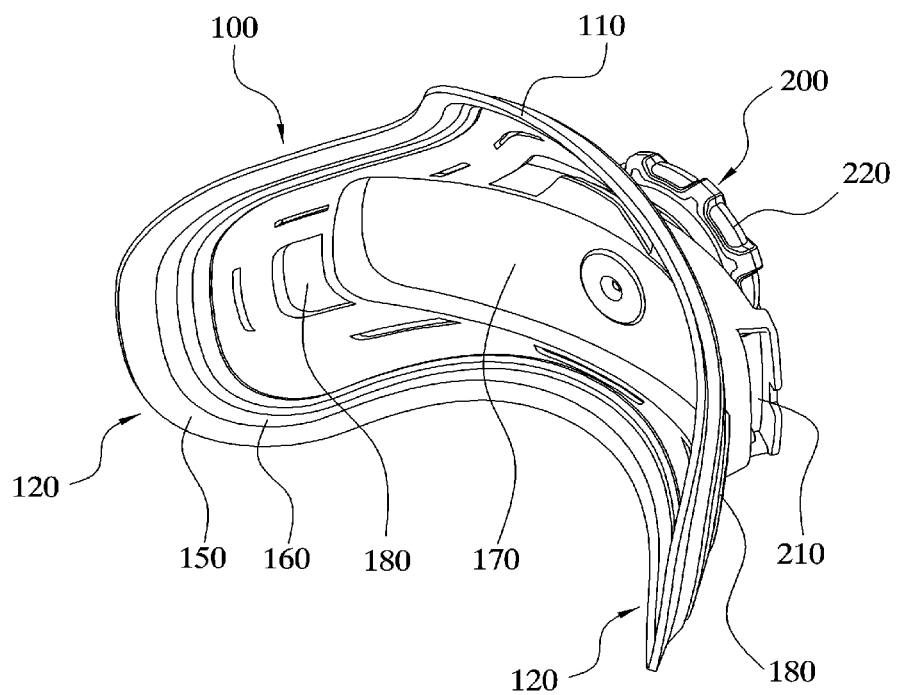
FIG. 8 is a perspective view illustrating the structure of the cushion pad for head bands in accordance with the present invention.

A cushion pad for head bands in accordance with the present invention includes, as exemplarily shown in FIGS. 1 to 8, a pad unit 100 closely adhered to the back of a worker's head and an adjustment unit 200 to adjust the length of a head band.

The present invention relates to a cushion pad for head bands which is installed at the rear part of a head band worn on a worker's head so as to support the back of the worker's head while adjusting the length of the head band, and the cushion pad for head bands includes the pad unit 100 having a concave spherical-shaped surface closely adhered to the back of the worker's head and provided with a first prop 110 extending from the center of the pad unit 100 to support the upper central region of the back of the worker's head and second props 120 extending from the center of the pad unit 100 to support both lower side regions of the back of the worker's head, and the adjustment unit 200 formed at the rear of the center of the pad unit 100 and provided with through holes formed at both sides thereof to receive both rear ends of the head band and a rotary lever installed at the rear of the middle between the through holes to pressurize and thus fix the head band.

The pad unit 100 has a concave spherical-shaped surface closely adhered to the back of the worker's head and is provided with the first prop 110 extending from the center of the pad unit 100 to support the upper central region of the back of the worker's head and the second props 120 extending from the center of the pad unit 100 to support both lower side regions of the back of the worker's head. That is, the pad unit 100 has a spherical surface closely adhered to the spherical surface of the back of the worker's head so as to conveniently and stably support the back of the worker's head, and is formed to have a tripod structure having the first prop 110 and the second props 120 so as to stably support the worker's head and to allow the worker to conveniently move his/her neck. Particularly, a curved surface, which is concave upwards for free movement of the neck, is formed between the second props 120.

In accordance with one embodiment of the present invention, a radius R1 of the center of the spherical surface of the pad unit 100 in the leftward and rightward directions of 70 to 110 mm and a radius R2 of the center of the spherical surface of the pad unit 100 in the upward and downward directions of 85 to 130 mm. Here, the radius R1 may be about 85 mm, and the radius R2 may be about 120 mm.

A curved surface for convenient neck movement is formed between the second props 120 of the pad unit 100. A radius R3 of the curved surface between the second props 120 of the pad unit 100 as seen from the bottom is 35 to 80 mm and a radius R4 of the curved surface between the second props 120 of the pad unit 100 as seen from the front is 50 to 100 mm. Here, the radius R3 may be about 60 mm and the radius R4 may be about 70 mm.

A distance D1 from the center of the pad unit 100 to the end of the first prop 110 of the pad unit 100 as seen from the front is 40 to 80 mm. Here, the distance D1 may be about 55 mm.

A distance D2 from the center of the pad unit 100 to the lower end of the pad unit 100 between the second props 120 is 15 to 50 mm, and a distance D3 from the center of the pad unit 100 to the lower ends of the second props 120 is 30 to 70 mm. Here, the distance D2 may be about 40 mm, and the distance D3 may be about 45 mm.

The adjustment unit 200 is formed at the rear of the center of the pad unit 100, and is provided with through holes 210 formed through both sides thereof to receive both rear ends of the head band and a rotary lever 220 installed at the rear of the middle between the through holes 210 to adjust the length of the head band. Therefore, after both rear ends of the head band are inserted into the through holes 210 and then the length of the head band is adjusted, the rotary lever 220 is rotated to pressurize the head band in the through holes 210 and thus fixes the adjusted length of the head band.

In order to prevent a head band from sliding on hair, a cushion pad for head bands in accordance with another embodiment of the present invention is formed by double injection molding using a hard material and a soft material.

Further, a pad unit 100 has a concave spherical-shaped surface closely adhered to the back of a worker's head, and an edge pressure part 150 including first and second props 110 and 120 extending from the center of the pad unit 100 to support the upper central region and both side regions of the back of the worker's head has both a pressurizing function and a cushioning function.

The edge pressure part 150 formed of a soft material includes an end part having a small thickness and formed at the end thereof and a plurality of edge protrusions 160 formed at the center thereof so as to apply pressure. A hard center part 170 provided with a central groove formed at the center thereof and extending to the second props 120 supporting both sides of the back of the worker's head to support the second props 120 formed of a soft material is formed. Otherwise, air vent holes 180 to rapidly exhaust air therethrough without pressure applied thereto, when the cushion pad is worn on the worker's head, are formed through the surfaces of the second props 120, and cause air to smoothly enter into and exit from the worker's head therethrough so that the wearing part of the worker's head within the cushion pad is dehumidified.

The first and second props 110 and 120 having the above-described triangular structure of the pad unit 100 are formed to have the respective radii R1, R2, R3 and R4. That is, the radius R1 of the center of the spherical surface of the pad unit 100 in the leftward and rightward directions is 70 to 110 mm, the radius R2 of the center of the spherical surface of the pad unit 100 in the upward and downward directions is 85 to 130 mm, the radius R3 of a curved surface formed between the second props 120 for convenient neck movement as seen from the bottom is 35 to 80 mm and the radius R4 of the curved surface as seen from the front is 50 to 100 mm.

The cushion pad for head bands is selectively applied to a ski helmet, a bicycle helmet, a motorcycle helmet, virtual reality goggles, a safety helmet, an industrial helmet, a safety face shield and a welding helmet.

The above-described cushion pad for head bands has an ergonomic structure and a minimized weight so as to be fixed to a worker's head.

As described above, the cushion pad for head bands in accordance with the present invention is installed at the rear part of a head band of a welding mask so as to stably support the back of a worker's head while adjusting the length of the head band, thereby allowing a worker to more conveniently and stably wear the welding mask.

As apparent from the above description, a cushion pad for head bands in accordance with the present invention is installed at the rear part of a head band of a welding mask, etc. so as to stably support the back of a worker's head while adjusting the length of the head band, thereby allowing a worker to more conveniently and stably wear the welding mask, etc. Further, the cushion pad for head bands in accordance with the present invention stably supports and surrounds the lower part of the back of the worker's head so as not to be removed from the worker's head in spite of strong motion of the worker's head and may thus be conveniently used by the worker.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A cushion pad for head bands, installed at the rear part of a head band worn on a worker's head so as to support the back of the worker's head while adjusting the length of the head band, the cushion pad for head bands including:
   a pad unit having a concave spherical-shaped surface closely adhered to the back of the worker's head and provided with a first prop extending from the center of the pad unit to support the upper central region of the back of the worker's head and second props extending from the center of the pad unit to support both lower side regions of the back of the worker's head; and
   an adjustment unit formed at the rear of the center of the pad unit and provided with through holes formed at both sides thereof to receive both rear ends of the head band and a rotary lever installed at the rear of the middle between the through holes to pressurize and thus fix the head band.

2. The cushion pad for head bands according to claim 1, wherein a radius R1 of the center of the spherical surface of the pad unit in the leftward and rightward directions is 70 to 110 mm, and a radius R2 of the center of the spherical surface of the pad unit in the upward and downward directions is 85 to 130 mm.

3. The cushion pad for head bands according to claim 1, wherein a radius R3 of a curved surface formed between the second props as seen from the bottom is 35 to 80 mm, and a radius R4 of the curved surface as seen from the front is 50 to 100 mm.

4. The cushion pad for head bands according to claim 1, wherein a distance D1 from the center of the pad unit to the end of the first prop as seen from the front is 40 to 80 mm, a distance D2 from the center of the pad unit to the lower end of the pad unit between the second props is 15 to 50 mm, and a distance D3 from the center of the pad unit to the lower ends of the second props is 30 to 70 mm.

5. The cushion pad for head bands according to claim 1, wherein the pad unit is formed by double injection molding using a hard material and a soft material so as to prevent the head band from sliding on hair.

6. The cushion pad for head bands according to claim 1, wherein the pad unit includes an edge pressure part formed of a soft material and a hard center part, wherein:
   the edge pressure part includes an end part having a small thickness and a plurality of edge protrusions formed at the center of the edge pressure part so as to apply pressure thereto; and
   the hard center part is provided with a central groove formed at the center thereof and extending to the second props supporting both sides of the back of the worker's head to support the second props formed of the soft material.

7. The cushion pad for head bands according to claim 1, wherein air vent holes to rapidly exhaust air therethrough without pressure applied thereto are formed through the surfaces of the second props, and cause air to smoothly enter into and exit from the worker's head therethrough so that the wearing part of the worker's head within the cushion pad is dehumidified.

8. The cushion pad for head bands according to claim 1, wherein the first and second props having a triangular structure of the pad unit are formed to have respective radii R1, R2, R3 and R4,
   wherein the radius R1 of the center of the spherical surface of the pad unit in the leftward and rightward directions is 70 to 110 mm, the radius R2 of the center of the spherical surface of the pad unit the upward and downward directions is 85 to 130 mm, the radius R3 of a curved surface, formed between the second props of the pad unit for convenient neck movement, as seen from the bottom is 35 to 80 mm and the radius R4 of the curved surface as seen from the front is 50 to 100 mm.

9. The cushion pad for head bands according to claim 1, being selectively applied to a ski helmet, a bicycle helmet, a motorcycle helmet, virtual reality goggles, a safety helmet, an industrial helmet, a safety face shield and a welding helmet.

10. The cushion pad for head bands according to claim 1, wherein the first prop extends vertically from the center of the pad unit to support the upper central region of the back of the worker's head.

11. The cushion pad for head bands according to claim 10, wherein the cushion pad matches horizontal and vertical sizes of the back of the worker's head.

12. The cushion pad for head bands according to claim 11, wherein the cushion pad ergonomically surrounds the back of the worker's head.

13. The cushion pad for head bands according to claim 12, wherein the cushion pad surrounds the lower part of the back of the worker's head.

14. The cushion pad for head bands according to claim 1, wherein:
   a radius R1 of the center of the spherical surface of the pad unit in the leftward and rightward directions is 70 to 110 mm;
   a radius R2 of the center of the spherical surface of the pad unit in the upward and downward directions is 85 to 130 mm;
   a radius R3 of a curved surface formed between the second props as seen from the bottom is 35 to 80 mm; and
   a radius R4 of the curved surface as seen from the front is 50 to 100 mm.

15. The cushion pad for head bands according to claim 14, wherein:
   a distance D1 from the center of the pad unit to the end of the first prop as seen from the front is 40 to 80 mm;
   a distance D2 from the center of the pad unit to the lower end of the pad unit between the second props is 15 to 50 mm; and
   a distance D3 from the center of the pad unit to the lower ends of the second props is 30 to 70 mm.

16. The cushion pad for head bands according to claim 15, wherein the first and second props have a triangular structure.

* * * * *